(12) United States Patent
Kaiser et al.

(10) Patent No.: US 8,071,966 B2
(45) Date of Patent: Dec. 6, 2011

(54) CONTROL DEVICE FOR CONTROLLING AN IRRADIATION PROCEDURE, PARTICLE THERAPY UNIT, AND METHOD FOR IRRADIATING A TARGET VOLUME

(75) Inventors: Werner Kaiser, Erlangen (DE); Peter van Haβelt, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 455 days.

(21) Appl. No.: 12/181,878

(22) Filed: Jul. 29, 2008

(65) Prior Publication Data
US 2009/0032742 A1 Feb. 5, 2009

(30) Foreign Application Priority Data
Aug. 1, 2007 (DE) .................. 10 2007 036 035

(51) Int. Cl.
*G02B 5/00* (2006.01)
*G21K 1/00* (2006.01)
*H01J 1/52* (2006.01)
*H01J 29/46* (2006.01)

(52) U.S. Cl. ............... 250/505.1; 250/503.1; 250/492.1; 600/1; 600/9

(58) Field of Classification Search ............... 250/503.1, 250/505.1, 492.1, 492.3; 600/1, 9
See application file for complete search history.

(56) References Cited

U.S. PATENT DOCUMENTS

| 5,039,867 | A | 8/1991 | Nishihara et al. |
| 5,625,331 | A | 4/1997 | Yamada et al. |
| 6,034,377 | A | 3/2000 | Pu |
| 6,717,162 | B1 | 4/2004 | Jongen |
| 6,891,177 | B1 | 5/2005 | Kraft et al. |
| 2004/0227104 | A1* | 11/2004 | Matsuda et al. ........... 250/492.1 |
| 2006/0033042 | A1 | 2/2006 | Groezinger et al. |
| 2007/0262269 | A1* | 11/2007 | Trbojevic .................. 250/492.3 |
| 2007/0295910 | A1 | 12/2007 | Harada |

FOREIGN PATENT DOCUMENTS

| DE | 11 2005 002 154 T5 | 4/2008 |
| EP | 0 826 394 A2 | 3/1998 |
| EP | 1477206 | 11/2004 |
| EP | 1 733 757 A2 | 12/2006 |
| JP | 10-314323 | 12/1998 |
| WO | WO 00/40064 A2 | 7/2000 |

(Continued)

OTHER PUBLICATIONS

European Office Action dated Jan. 25, 2010 with English translation.

(Continued)

*Primary Examiner* — Robert Kim
*Assistant Examiner* — Brooke Purinton
(74) *Attorney, Agent, or Firm* — Lempia Summerfield Katz LLC

(57) ABSTRACT

The present embodiments relate to a control device for controlling an irradiation procedure, which is designed in such a way that a target volume is irradiated by at least two irradiation procedures. In each irradiation procedure, an energy of a particle beam is varied in such a way that the target volume is irradiated layer-wise in layers that are spatially arranged one behind another. A sequence in which the layers of the target volume are irradiated in one of the irradiation procedures is varied from irradiation procedure to irradiation procedure, in terms of a direction of incidence of the particle beam.

17 Claims, 3 Drawing Sheets

FOREIGN PATENT DOCUMENTS

WO    WO 2005/120641    12/2005
WO    WO 2006 082650 A1    8/2006

OTHER PUBLICATIONS

German Office Action dated Jun. 12, 2008 with English translation.
European Office Action dated Nov. 6, 2008 with English translation.
European Search Report dated Oct. 28, 2008 with English translation.
Haberer et al., "Magnetic Scanning System for Heavy Ion Therapy," Nuclear Instruments and Methods in Physics Research A330 (1993), pp. 296-305.

* cited by examiner

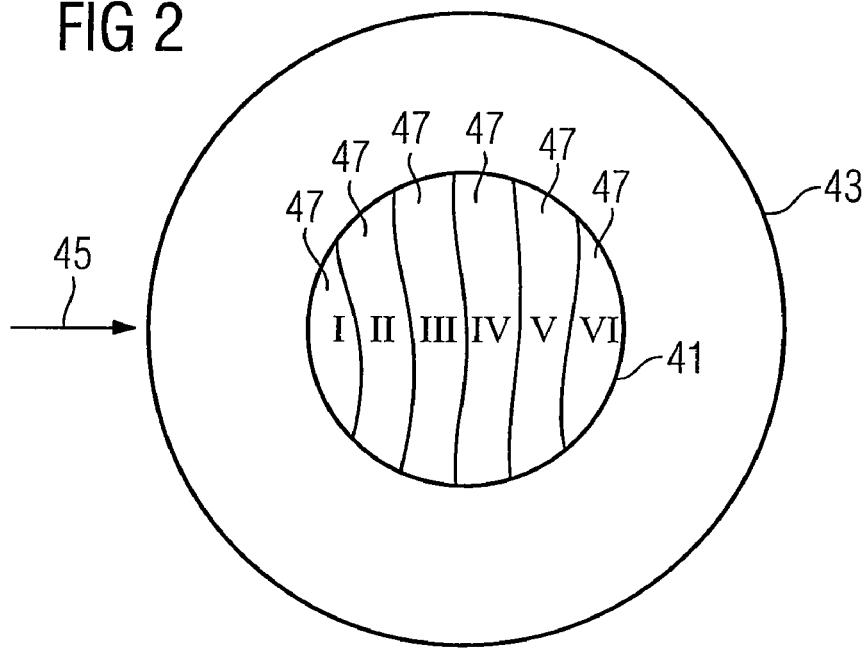
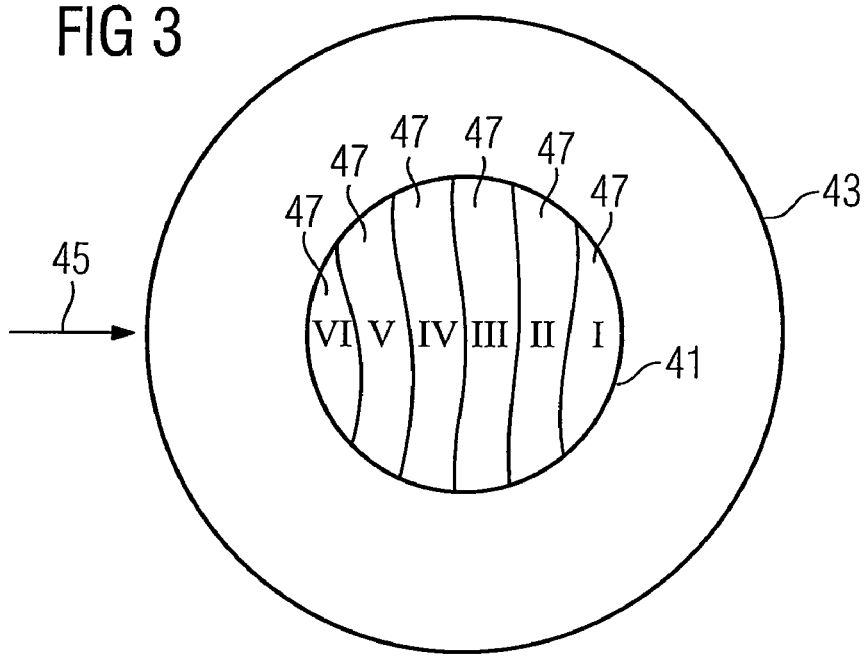

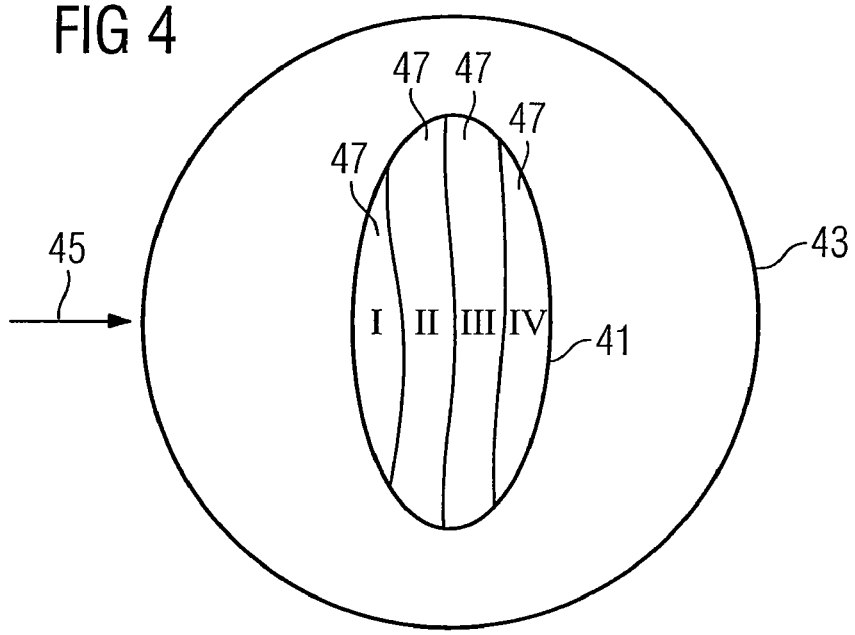
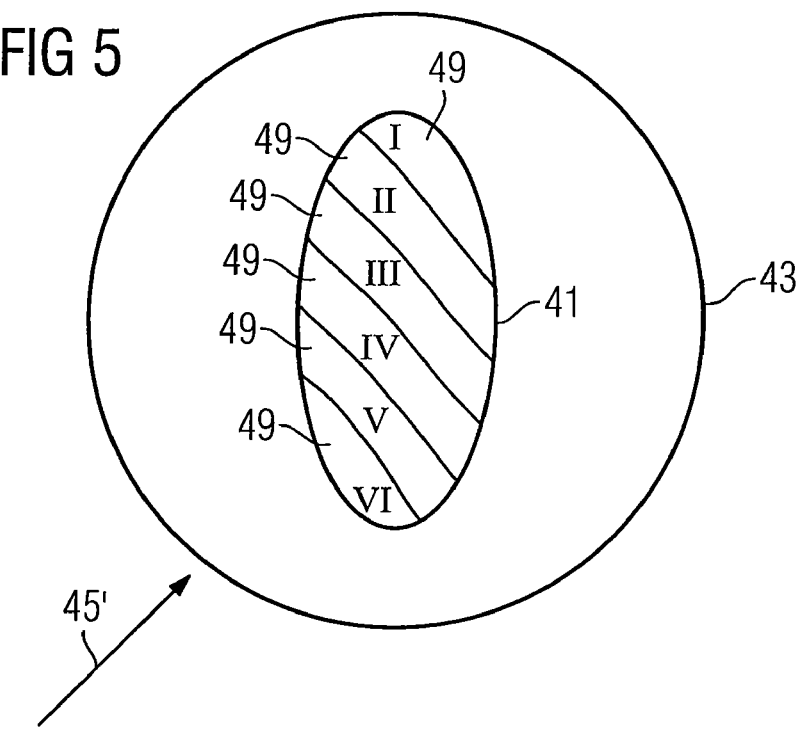

CONTROL DEVICE FOR CONTROLLING AN IRRADIATION PROCEDURE, PARTICLE THERAPY UNIT, AND METHOD FOR IRRADIATING A TARGET VOLUME

The present patent document claims the benefit of the filing date of German Patent Document DE 10 2007 036 035.7, filed Aug. 1, 2007, which is hereby incorporated by reference.

BACKGROUND

The present embodiments relate to a control device for controlling an irradiation procedure in a particle therapy unit, a particle therapy unit, and a method for irradiating a target volume.

Particle therapy is used for the treatment of tissue, such as tumor diseases. Irradiation methods used in particle therapy may, however, also be used in non-therapeutic fields. The non-therapeutic fields include, for example, research work in the context of particle therapy, carried out on non-living phantoms or bodies, or irradiation of materials. In such methods, charged particles are accelerated to high energies, formed into a particle beam and directed onto an object that is to be irradiated. The particle beam penetrates the object and releases its energy in a defined location, which leads to the destruction of the tissue in the defined location. The particles used are protons and carbon ions, but pions, helium ions and other types of ions are also used.

Compared to irradiation methods using x-ray beams, particle therapy has the distinguishing feature that the particles in the particle beam release the main part of their energy in an area that can be relatively well defined within the target volume. Exactly where the particle beam interacts with the target volume, for example, at what depth of the target volume in terms of the direction of the beam, depends mainly on the energy of the particle beam. The higher the energy of the particle beam, the further the particle beam penetrates into the target volume and the deeper is the area in which the particles discharge their energy onto the target volume. Accordingly, a target volume that is to be irradiated within an object may be irradiated with relative precision. Irradiation in surrounding areas may be avoided.

A target volume may be irradiated in a plurality of layers. The target volume is irradiated in a plurality of layers when the target volume in the direction of the beam is so large that the layer in which particles release their energy with a defined energy is so thin that the target volume cannot be captured by the particle beam by particles with the defined energy. Irradiation of the target volume often ensues in layers, the energy of the particles being adjusted in each layer to the depth of the layer in the object that is to be irradiated.

The energy of the particles is adjusted immediately in front of the object that is to be irradiated, and before the irradiation procedure, for example, in the area of the accelerator. The particles are accelerated to an energy that is required for irradiation, or in the area of the high-energy beam transport system with which particles are transported from an accelerator to an irradiation chamber.

Complex irradiation procedures, such as irradiating a plurality of layers, require complex control of the particle therapy unit and synchronization of the energy of the particle beam with the layers that are to be irradiated.

SUMMARY AND DESCRIPTION

The present embodiments may obviate one or more of the drawbacks or limitations inherent in the related art. For example, in one embodiment, a control device controls an irradiation procedure in a particle therapy unit, such that there is a low load on the components of a particle therapy unit even in complex irradiation procedures with a complex synchronization of the energy of the particle beam. In another example, a method for irradiating a target volume even in complex irradiation procedures with a complex synchronization of the energy of the particle beam is provided. The method places only a slight load on the components of a particle therapy unit.

The control device for controlling an irradiation procedure in a particle therapy unit is designed in such a way that a target volume is irradiated by at least two irradiation procedures. The irradiation procedures vary an energy of a particle beam in such a way that the target volume is irradiated layer-wise in layers that are arranged spatially one behind the other in the direction of the beam. A sequence in which the layers of the target volume are irradiated in one of the irradiation procedures is varied from irradiation procedure to irradiation procedure (e.g., in terms of a direction of incidence of the particle beam).

An irradiation procedure is an irradiation session in which at least some of the layers of the target volume are irradiated successively one after another. The irradiation of the layers ensues in one direction during an irradiation procedure (in terms of the direction of the beam), for example, either in the direction of the beam or against the direction of the beam.

Since the layers of a target volume that are always irradiated in the same sequence in a plurality of irradiation procedures, the energy of the particle beam is adjusted accordingly. The adjustment of the energy may lead to an unfavorable load being placed on the components of a particle therapy unit, such as in the transition from one irradiation procedure to the next irradiation procedure, for example, if the change in energy involves large jumps. If, for example, layers of a target volume are irradiated in one direction (e.g., from front to back in terms of the direction of the beam), the energy in the transition from one irradiation procedure to the next irradiation procedure has to be regulated from a maximum value to a minimum value. The abrupt jump in the energy of the particle beam leads to an unfavorable load being placed on the components of a particle therapy unit.

When superconducting magnets are used to direct the beam in a particle therapy unit, a magnetic field generated by said superconducting magnets has to be synchronized with the energy of the particle beam.

When the energy of the particle beam changes abruptly, the rapid adjustment of the magnetic field leads to alternating field losses (also referred to hereafter as "AC losses"). Since AC losses lead to increased cooling capacity being required, components of the particle therapy unit as a whole are subjected to heavy loads. The problem may be solved either by providing increased cooling capacity or by the change in the magnetic field being effected slowly. The solutions may have increased costs or require increased time being required in complex irradiation procedures. The heavy load on the components of a particle therapy unit is not just limited to superconducting magnets, however, even if in this case the load is more clearly evident as a result of the clearly increased cooling capacity required.

The control device is operable to vary, from irradiation procedure to irradiation procedure, the sequence in which the layers are irradiated in an irradiation procedure. Large transitions or jumps in the energy of the particle beam may be avoided.

The sequence in which the layers are irradiated in an irradiation procedure may be changed in such a way that, in the transition from irradiation procedure to irradiation procedure, the identical layer or adjacent layers are irradiated. Directly adjacent layers may be irradiated.

The energy of the particle beam is changed only to a slight extent from layer to layer and from irradiation procedure to irradiation procedure. The sequence of layers that can be irradiated in one irradiation procedure may be reversed in the next irradiation procedure, for example.

In one embodiment, the control device is designed such that the sequence of layers that are irradiated in an irradiation procedure alternates from irradiation procedure to irradiation procedure in terms of the direction of incidence. If, in a first irradiation procedure, for example, the layers are irradiated from front to back in terms of the direction of the beam, this direction is reversed in the next irradiation procedure so that the layers are now irradiated from back to front. The energy of the particle beam changes from a minimum value to a maximum value and then from the maximum value back to the minimum value. The load that is placed on components of the particle therapy unit is comparatively low.

The irradiation of one of the layers may be achieved using a scattering method or using a scanning method. In the scattering method, the lateral extension of the particle beam is extended and adapted to the dimensions of the layer that is to be irradiated using a collimator, for example. In the scanning method, the particle beam retains a relatively small lateral extension, of a few millimeters, for example, and is directed successively to various points in the layer so that the layer is "scanned" by the particle beam in a grid, for example.

In the at least two irradiation procedures, it is possible to irradiate the same layers in the target volume, or also alternatively for different layers in the target volume to be irradiated. For example, the layers in the target volume may be repositioned from irradiation procedure to irradiation procedure, if, for example, a different irradiation field is irradiated in each irradiation procedure.

The direction of incidence of the particle beam may remain the same or may be varied from irradiation procedure to irradiation procedure.

The control device does not have to be a sealed unit in a particle therapy unit. The control device may be subdivided into individual partial devices that provide the functionality of the control device in their combined action. For example, the control device may be achieved by a control device to control the energy of the particle beam, and by a control device to convert control commands stored in a therapy plan. The device being may be operable to vary the irradiation of a sequence of layers to be irradiated from irradiation procedure to irradiation procedure.

In one embodiment, a particle therapy unit may include a particle source for the generation of particles, an accelerator to accelerate the particles and to provide a high-energy particle beam, a high-energy beam transport system to direct a particle beam formed of the accelerated particles into an irradiation chamber, an energy adjusting device with which the energy of the particle beam can be adjusted, and a control device to control an irradiation procedure. The control device is operable to control the energy adjusting device.

The energy adjusting device may control the accelerator, for example, in such a way that the particles are accelerated such that a desired energy of the particle beam is obtained.

The accelerator may be, for example, a synchrotron or a cyclotron. A synchrotron may adjust the energy of a particle beam. A cyclotron may adjust the energy of the particle beam, using an Energy Selection System for example, after acceleration of the particles.

The accelerator or the high-energy beam transport system may include at least one superconducting magnet. The superconducting magnet generates only slight AC losses even if complex irradiation procedures are carried out. The energy adjusting device controls the energy of the particle beam in the direction of the beam in front of the superconducting magnet, for example, before the particle beam is directed by the magnetic field of the superconducting magnet. The magnetic field is again synchronized with the energy of the particle beam. For example, the control device, which is to control the irradiation process with which the energy of the particle beam is adjusted, at the same time controls the magnetic field during an irradiation procedure.

A method for controlling the energy of a particle beam during an irradiation of a target volume is provided. The method may be used to irradiate a target volume using at least two irradiation procedures. The energy of a particle beam is varied in such a way that in the two irradiation procedures, the target volume is irradiated layer-wise in layers that are spatially arranged one behind another, and a sequence in which the layers of the target volume are irradiated in one of the irradiation procedures is varied from irradiation procedure to irradiation procedure, in terms of a direction of incidence of the particle beam.

The sequence of layers will run alternately from irradiation procedure to irradiation procedure in terms of the respective direction of incidence of the particle beam. The energy of the particle beam may be adjusted before the particle beam is directed by a superconducting magnet of an accelerator or of a high-energy beam transport system. The magnetic field of the superconducting magnet is adjusted to the energy of the particle beam.

BRIEF DESCRIPTION OF THE FIGURES

FIG. 2 and FIG. 3 show the irradiation in layers of a target volume in two consecutive irradiation procedures, the same layers being irradiated and a particle beam with the same direction of incidence being used, and FIG. 4 and FIG. 5 show the irradiation in layers of a target volume during two consecutive irradiation procedures, different layers being irradiated in each case with a particle beam with a modified direction of incidence.

DETAILED DESCRIPTION

Figure 1:
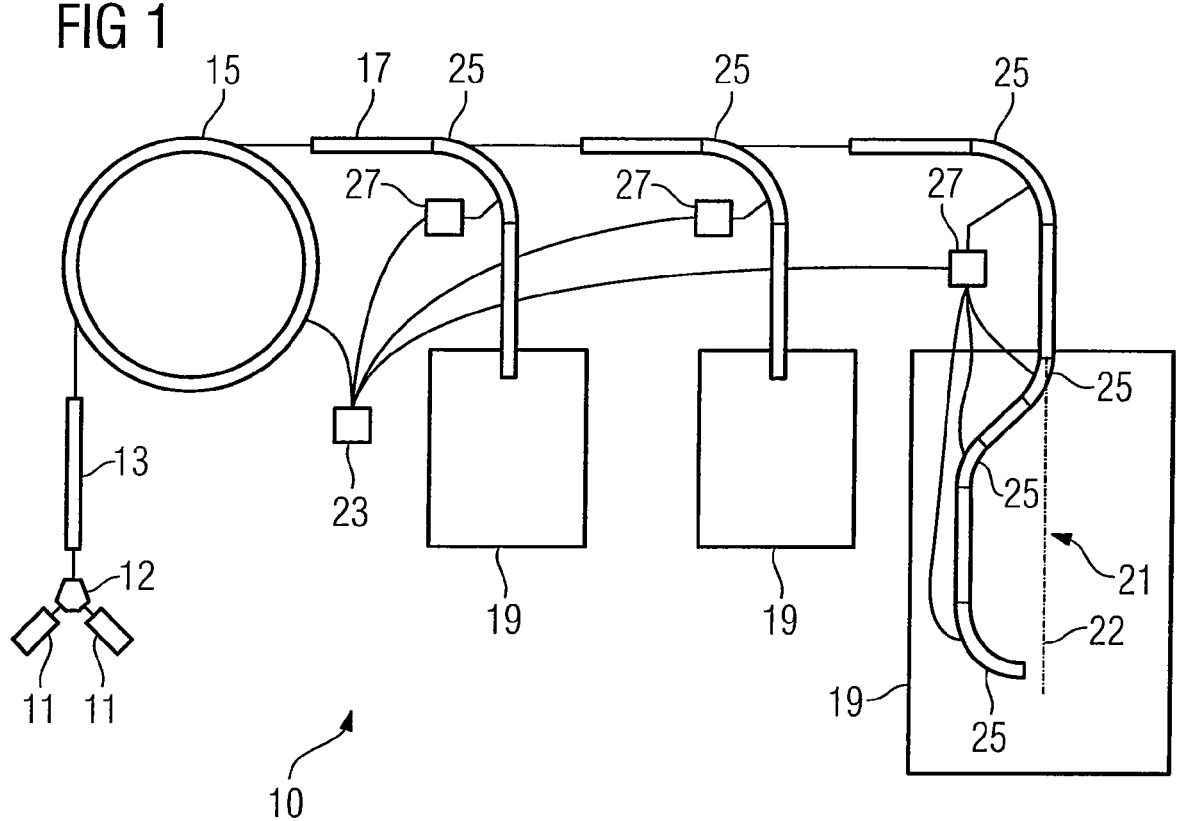
FIG. 1 shows a schematic design for a particle therapy unit.

FIG. 1 shows a particle therapy unit 10. The particle therapy unit 10 is used for irradiation of a body, such as a tumor-diseased tissue, using a particle beam.

The particles may include ions, such as protons, pions, helium ions, carbon ions or other types of ions. The particles may be generated in a particle source 11. If, as shown in FIG. 1, there are two particle sources 11, which generate two different types of ions, it is possible to switch between the two types of ions within a short period of time. For example, a switching magnet 12, which is arranged between the ion sources 11 and a pre-accelerator 13 is used for switching. The particle therapy unit 10 may be operated with protons and with carbon ions at the same time for example.

The ions generated by the or by one of the ion sources 11 and optionally selected using the switching magnet 12 are accelerated in the pre-accelerator 13 to a first energy level. The pre-accelerator 13 is, for example, a linear accelerator (LINAC: short for "LINear ACcelerator"). The particles are fed into an accelerator 15, for example, a synchrotron or cyclotron. The particles are accelerated in the accelerator 15 to high energies such as those required for irradiation. After the particles have left the accelerator 15, a high-energy beam transport system 17 directs the particle beam to one or to a plurality of irradiation chambers 19. In an irradiation chamber 19, the accelerated particles are directed onto a body that is to be irradiated. Depending on the configuration, the accelerated particles may be directed onto a body from a fixed direction (e.g., a "fixed beam" chambers) or from various directions by a gantry 21 that is rotatable around an axis 22.

In one embodiment, the energy of the particle beam may be adjusted, for example, by the accelerator 15 being actuated accordingly. A precise adjustment of the energy of the particle beam may take place in the treatment room 19, for example, directly before the particle beam falls onto an object that is to be irradiated.

The energy of the particle beam is controlled by a control device 23 that actuates the appropriate components with which the energy of the particle beam is adjusted. The control device 23 may, for example, actuate the accelerator 15 such that the particles are accelerated to a desired energy. The control device 23 consequently varies the energy of the particle beam, so that in complex irradiation procedures an irradiation may be achieved in layers. The layer to be irradiated is determined by the energy of the particle beam. The control device 23 is configured here in such a way that a sequence in which the layers of the target volume are irradiated is varied from irradiation procedure to irradiation procedure.

A plurality of magnetic components 25 are used in a particle therapy unit for the acceleration, formation and deflection of the particle beam. Some of the magnetic components 25, such as dipolar magnets, are shown in FIG. 1. At least one of the dipolar magnets may be used in a superconductive manner. For example, a dipolar magnet may be a dipolar magnet of the gantry or a dipolar magnet of the high-energy beam transport system.

The control device 23 is operable to control the magnetic components 25, by which the particle beam is directed such that the magnetic field of the magnetic components 25 that is required for correct direction of the beam is synchronized with the energy of the particle beam. The control may be achieved directly or indirectly by the control device 23 transmitting appropriate control commands to further control devices 27 for the corresponding magnetic components.

With superconducting magnetic components, such as a superconducting dipolar magnet, for example, an adaptation of the magnetic field involves what is known as an AC loss. The AC loss is the greater, the faster and more intensively such an adaptation is achieved.

The control device 23 is operable to provide an irradiation of a target volume, as explained hereafter in more detail with reference to FIG. 2 to FIG. 5.

A particle therapy unit 10, as shown in FIG. 1, is typical of many particle therapy units, but can also deviate therefrom. For example, a particle therapy unit may have only an irradiation chamber. If a cyclotron is used for the acceleration of particles, an energy selection system with which the energy of the particle beam may be adjusted can also be arranged in the high-energy beam transport system.

FIG. 2 shows a spherical target volume 41, which is located in an object that is to be irradiated 43. The arrow 45 in front of the object 43 shows the direction of the particle beam. An adjustment of the spatial relationship between the direction of the particle beam and the object that is to be irradiated may be achieved, for example, by directing the particle beam using a moveable gantry. Alternatively and/or additionally, the adjustment may be achieved by positioning the object in terms of the particle beam, for example, using a positioning device designed as a robotic arm.

The target volume 41 that is to be irradiated has a dimension in the direction of the beam such that the target volume 41 is not completely captured by a particle beam having a defined energy. In order to irradiate the target volume 41 completely, however, the energy of the particle beam is varied successively, so that a layer 47 of the target volume 41 is irradiated in each case. The form of the layers 47 may deviate from a parallel arrangement. The non-parallel arrangement may be caused, for example, by a non-homogeneous distribution of the tissue within the object to be irradiated 43 or within the target volume 41. Adaptation of the lateral extension of the particle beam to the respective layer to be irradiated 47 can take place in various ways. In the scattering method, for example, an expanded particle beam may be adapted by collimators to the extension of the respective layer that is to be irradiated 47. In the scanning method, a needle-shaped particle beam may be directed successively onto various points within the layer that is to be irradiated 47 until irradiation of the whole layer 47 has been achieved.

During an irradiation procedure, at least some of the layers 47, and preferably all the layers 47, are irradiated in a direction in terms of the direction of incidence of the particle beam. The Roman numerals I to VI within the layers 47 denote the sequence in which the layers are irradiated during the irradiation procedure shown in FIG. 2. First the layer 47 (Roman numeral I), which is at the front in the direction of the beam is irradiated. Next, successive layers that are located at greater and greater depth are irradiated until finally the layer 47 (denoted by the Roman numeral I), which is at the back in the direction of the beam is irradiated.

FIG. 3 shows the sequence of layers 47, as are irradiated in the next irradiation procedure. The sequence of layers 47 is varied, such that in the present irradiation procedure the layer 47 with the Roman numeral I is irradiated first. The layer is the furthest back in the direction of the beam and was the last to be irradiated in the previous irradiation procedure (shown in FIG. 2). The layers 47 are irradiated next, starting with the layer that is at the back in the direction of the beam, in succession, moving towards the front. The frontmost layer 47 with the Roman numeral VI is irradiated. Like in FIG. 2, the Roman numerals I to VI within the layers denote the sequence of irradiation for the layers.

The energy of the particle beam may be changed only slightly during an irradiation from layer 47 to layer 47 and during an irradiation from irradiation procedure (shown by FIG. 2) to irradiation procedure (shown by FIG. 3), so that superconducting components of the accelerator and/or of the high-energy beam transport system only have to be adapted slightly to the change in the energy of the particle beam. The loads generated for components, such as AC losses, only occur to a minimum extent.

In the example shown in FIG. 2 and FIG. 3, the same layers 47 are always irradiated. For example, the same target volume 41 may be scanned a plurality of times in layers. In the example shown in FIG. 4 and FIG. 5, a target volume 41 may be irradiated from one direction (shown by the arrow 45) in one irradiation procedure and from a different direction (shown by the arrow that has been changed 45') in the next irradiation procedure. Since the target volume 41 shown here is longitudinal in shape, four layers 47 are necessary for the irradiation of the target volume 41 in one direction (FIG. 4).

The six further layers 49 are necessary for the irradiation of the target volume in the other direction (FIG. 5).

The sequence of layers 47 or 49 may be varied from irradiation procedure to irradiation procedure. In the irradiation procedure shown by FIG. 4, the layers 47 are irradiated from front to back—in terms of the direction of the beam. In FIG. 4, the sequence is indicated by the Roman numerals I to IV in the layers. In FIG. 5, the sequence of the further layers 49 is reversed so that the further layers 49 are irradiated from back to front. The Roman numerals I to VI in the further layers 49 denote the sequence of irradiation of the further layers 49. The energy of the particle beam only has to be slightly adapted in the transition from one irradiation procedure (shown by FIG. 4) to the next irradiation procedure (shown by FIG. 5). The adaptation is far slighter than an adaptation that would be necessary if the sequence of the irradiation of the layers 47 or 49 were to be left as it was from irradiation procedure to irradiation procedure in terms of the direction of the beam.

The irradiation procedures, as illustrated in FIG. 2 to FIG. 5, may be varied. For example, it is not absolutely essential for all the layers of the target volume always to be irradiated in an irradiation procedure. It is possible, for example, for every second layer to be irradiated in an irradiation procedure and for the layers that have not yet been irradiated to be irradiated in the subsequent irradiation procedure, but this time in a reverse sequence.

With a transition from one irradiation procedure to the next, it is likewise not necessary for the same layer to be irradiated, as explained in FIG. 2 and FIG. 3. It is also possible, for example, for adjacent layers to be irradiated. There is only a slight variation in the energy of the particle beam.

The invention claimed is:

1. A control device for controlling an irradiation procedure in a particle therapy unit, the control device being configured to control at least two irradiation procedures of a target volume, the control device comprising:
    an energy variation controller configured to vary an energy of a particle beam in the at least two irradiation procedures in such a way that the target volume is irradiated layer-wise in layers that are spatially arranged one behind another,
    a sequence variation controller configured to vary a sequence, in which the layers of the target volume are irradiated in one of the at least two irradiation procedures, from a first of the at least two irradiation procedures to a second of the at least two irradiation procedures, in a direction of incidence of the particle beam, and
    an irradiation procedure controller configured to control the at least two irradiation procedures such that a sequence of layers that are irradiated in the first of the at least two irradiation procedures runs in an alternate direction from a sequence of layers that are irradiated in the second of the at least two irradiation procedures, with respect to the direction of incidence of the particle beam.

2. The control device as claimed in claim 1, wherein the sequence, in which the layers are irradiated in one of the irradiation procedures, is changed from the first irradiation procedure to the second irradiation procedure in such a way that in a transition from the first irradiation procedure to the second irradiation procedure, an identical layer is irradiated or adjacent layers are irradiated.

3. The control device as claimed in claim 1, wherein the same layers of the target volume are irradiated in the at least two irradiation procedures.

4. The control device as claimed in claim 1, wherein different layers of the target volume are irradiated in the at least two irradiation procedures.

5. The control device as claimed in claim 1, wherein the direction of incidence of the particle beam remains identical from the first irradiation procedure to the second irradiation procedure in the at least two irradiation procedures.

6. The control device as claimed in claim 1, wherein the direction of incidence of the particle beam is varied from the first irradiation procedure to the second irradiation procedure in the at least two irradiation procedures.

7. A particle therapy unit comprising:
    a particle source that is operable to generate particles,
    an accelerator that is operable to accelerate the particles and to provide a high-energy particle beam,
    a high-energy beam transport system that is operable to direct the high-energy particle beam formed of the accelerated particles into an irradiation chamber,
    an energy adjusting device that is operable to adjust an energy of the high-energy particle beam, and
    a control device that is configured to control at least two irradiation procedures of a target volume, the control device being configured to control the energy adjusting device to vary the energy of the high-energy particle beam in the at least two irradiation procedures in such a way that the target volume is irradiated layer-wise in layers that are spatially arranged one behind another,
    wherein the control device is configured to control the at least two irradiation procedures such that a sequence of layers that are irradiated in a first of the at least two irradiation procedures runs in an alternate direction to a sequence of layers that are irradiated in a second of the at least two irradiation procedures, with respect to a direction of incidence of the high-energy particle beam.

8. The particle therapy unit as claimed in claim 7, wherein the accelerator, the high-energy beam transport system, or the accelerator and the high-energy beam transport system include at least one superconducting magnet.

9. The particle therapy unit as claimed in claim 8, wherein the energy of the high-energy particle beam is adjusted using the energy adjusting device in the direction of incidence of the high-energy particle beam upstream of the at least one superconducting magnet, and
    wherein a magnetic field that is generated by the at least one superconducting magnet is synchronized with the energy of the high-energy particle beam.

10. A method for controlling energy of a particle beam during an irradiation of a target volume, in which the target volume is irradiated using at least two irradiation procedures, the method comprising:
    varying the energy of the particle beam such that in the at least two irradiation procedures, the target volume is irradiated layer-wise in layers that are spatially arranged one behind another, and a sequence, in which the layers of the target volume are irradiated in one of the at least two irradiation procedures, is varied from a first of the at least two irradiation procedures to a second of the at least two irradiation procedures, in a direction of incidence of the particle beam,
    wherein the sequence of layers that are irradiated in one irradiation procedure runs in an alternate direction from irradiation procedure to irradiation procedure in the direction of incidence of the particle beam.

11. The method as claimed in claim 10, wherein the sequence, in which the layers of the target volume are irradiated in one of the irradiation procedures, is varied in such a way that in a transition from the first of the at least two irradiation procedures to the second of the at least two irradiation procedures, an identical layer is irradiated or adjacent layers are irradiated.

12. The method as claimed in claim 10, wherein the same layers of the target volume are irradiated in the at least two irradiation procedures.

13. The method as claimed in claim 10, wherein different layers of the target volume are irradiated in the at least two irradiation procedures.

14. The method as claimed in claim 10, wherein the direction of incidence of the particle beam remains identical from the first of the at least two irradiation procedures to the second of the at least two irradiation procedures.

15. The method as claimed in claim 10, wherein the direction of incidence of the particle beam is varied from the first of the at least two irradiation procedures to the second of the at least two irradiation procedures.

16. The method as claimed in claim 10, wherein the energy of the particle beam is adjusted before the particle beam is directed by a superconducting magnet of an accelerator or of a high-energy beam transport system.

17. The method as claimed in claim 10, wherein the sequence, in which the layers of the target volume are irradiated in one of the irradiation procedures, is varied in such a way that in a transition from the first of the at least two irradiation procedures to the second of the at least two irradiation procedures, an identical layer is irradiated or adjacent layers are irradiated.

* * * * *